(12) United States Patent
Sajiki et al.

(10) Patent No.: US 7,795,166 B2
(45) Date of Patent: Sep. 14, 2010

(54) FUNCTIONAL GROUP-SELECTIVE HYDROGENATION CATALYST AND FUNCTIONAL GROUP-SELECTIVE HYDROGENATION METHOD

(75) Inventors: Hironao Sajiki, Gifu (JP); Tomohiro Maegawa, Philadelphia, PA (US); Kosaku Hirota, Nagoya (JP)

(73) Assignee: N.E. Chemcat Corporation, Tokyo (JP)

( * ) Notice: Subject to any disclaimer, the term of this patent is extended or adjusted under 35 U.S.C. 154(b) by 392 days.

(21) Appl. No.: 11/565,844

(22) Filed: Dec. 1, 2006

(65) Prior Publication Data

US 2007/0155617 A1 Jul. 5, 2007

(30) Foreign Application Priority Data

Dec. 2, 2005 (JP) ............................. 2005-349313

(51) Int. Cl.
| | |
|---|---|
| *B01J 31/00* | (2006.01) |
| *B01J 37/00* | (2006.01) |
| *B01J 27/02* | (2006.01) |
| *B01J 27/043* | (2006.01) |
| *B01J 27/045* | (2006.01) |
| *C08F 4/02* | (2006.01) |
| *C08F 4/60* | (2006.01) |
| *C07C 319/00* | (2006.01) |
| *C07C 321/00* | (2006.01) |
| *C07C 323/00* | (2006.01) |
| *C07C 381/00* | (2006.01) |
| *C07C 49/92* | (2006.01) |
| *C07C 5/10* | (2006.01) |
| *C07C 5/05* | (2006.01) |
| *C07C 5/02* | (2006.01) |
| *C07C 5/03* | (2006.01) |
| *C07F 5/00* | (2006.01) |
| *C07F 15/00* | (2006.01) |
| *C07F 17/02* | (2006.01) |

(52) U.S. Cl. ................ 502/122; 502/168; 502/216; 502/222; 502/223; 568/58; 556/1; 556/40; 556/136; 585/269; 585/271; 585/275; 585/277

(58) Field of Classification Search ............... 502/122, 502/168, 216, 222, 223; 568/58; 556/1, 556/40, 136; 585/269, 271, 275, 277

See application file for complete search history.

(56) References Cited

U.S. PATENT DOCUMENTS

| | | | | | |
|---|---|---|---|---|---|
| 3,251,892 | A | * | 5/1966 | Seefelder et al. | 585/273 |
| 3,715,404 | A | * | 2/1973 | Lindlar et al. | 568/903 |
| 3,947,495 | A | * | 3/1976 | Murib et al. | 502/168 |
| 4,236,024 | A | * | 11/1980 | Matsuda et al. | 560/244 |
| 4,520,129 | A | * | 5/1985 | Murtha | 502/222 |
| 5,821,397 | A | * | 10/1998 | Joly et al. | 585/262 |
| 7,453,003 | B1 | * | 11/2008 | Le-Khac | 549/533 |

FOREIGN PATENT DOCUMENTS

| | | | |
|---|---|---|---|
| JP | 5-213834 | | 8/1993 |
| JP | 05-213834 | * | 8/1993 |

OTHER PUBLICATIONS

Hironao Sajiki, et al., "Pd/C(en)-catalyzed regioselective hydrogenolysis of terminal epoxides to secondary alcohols", Chem. Commun., 1999, pp. 1041-1042.

* cited by examiner

*Primary Examiner*—Patricia L Hailey
(74) *Attorney, Agent, or Firm*—Oblon, Spivak, McClelland, Maier & Neustadt, L.L.P.

(57) ABSTRACT

A functional group-selective hydrogenation catalyst is provided, which is capable of selectively hydrogenating an aliphatic carbon-carbon double bond, aliphatic carbon-carbon triple bond, aromatic formyl group or aromatic nitro group contained in an organic compound. The catalyst includes a carrier, and palladium and an organic sulfur compound supported jointly thereon.

27 Claims, No Drawings

FUNCTIONAL GROUP-SELECTIVE HYDROGENATION CATALYST AND FUNCTIONAL GROUP-SELECTIVE HYDROGENATION METHOD

BACKGROUND OF THE INVENTION

1. Field of the Invention

The present invention relates to a functional group-selective hydrogenation catalyst and a functional group-selective hydrogenation method.

2. Description of the Prior Art

Compounds containing a plurality of different functional groups that undergo either hydrogenation or hydrogenolysis are numerous, and catalysts that are capable of achieving selective hydrogenation or hydrogenolysis of only a portion of those functional groups are already known. For example, the non-patent reference 1 discloses a carbon catalyst in which ethylenediamine and palladium are supported together on carbon black, and using this catalyst, it is possible to hydrogenate at least one functional group selected from the group consisting of an aliphatic carbon-carbon double bond, aliphatic carbon-carbon triple bond, aromatic formyl group and aromatic nitro group in the presence of at least one functional group selected from the group consisting of an O-benzyl group of a benzyl ether and a N-benzyloxycarbonyl group without causing hydrogenolysis of this functional group. However, the problem remains that an aromatic ketonic carbonyl group or an O-benzyl group of a benzyl ester still undergoes hydrogenolysis, if present.

The patent reference 1 discloses a method in which 2,4-dinitroaniline is subjected to a hydrogen reduction reaction in the presence of a palladium catalyst poisoned with sulfur, thereby selectively hydrogenating the nitro group at position-2 and producing a high yield of 1,2-diamino-4-nitrobenzene.

[Non-Patent Reference 1]
Chem. Commun., 1999, 1041
[Patent Reference 1]
Japanese Laid-open publication (kokai) No. Hei 05-213834

SUMMARY OF THE INVENTION

Accordingly, an object of the present invention is to provide a catalyst capable of selectively hydrogenating at least one functional group selected from the group consisting of an aliphatic carbon-carbon double bond, aliphatic carbon-carbon triple bond, aromatic formyl group and aromatic nitro group, such that even when the compound also contains an N-benzyloxycarbonyl group, O-benzyl group of a benzyl ether or any other general O-benzyl group including an O-benzyl group of a benzyl ester, aromatic ketonic carbonyl group, aromatic nitrile group, or aromatic ring-bonded halogen atom, these functional groups undergo no hydrogenation or hydrogenolysis. The invention also provides a method of producing the catalyst and a hydrogenation method that uses the catalyst.

MEANS FOR SOLUTION OF THE PROBLEMS

As a result of intensive investigation of palladium-based catalysts, the inventors of the present invention discovered that a catalyst in which an organic sulfur compound was supported together with palladium on a carrier exhibited a functional group-selective hydrogenation capability that was able to achieve the above object, and they were therefore able to complete the present invention.

In other words, the present invention provides a functional group-selective hydrogenation catalyst for an organic compound having at least one functional group selected from the group consisting of an aliphatic carbon-carbon double bond, aliphatic carbon-carbon triple bond, aromatic formyl group and aromatic nitro group, which functions as a selective hydrogenation catalyst for said functional group, said catalyst comprising a carrier, and palladium and an organic sulfur compound supported jointly thereon.

In addition, the present invention also provides a functional group-selective hydrogenation method, wherein an organic compound having at least one functional group selected from the group consisting of an aliphatic carbon-carbon double bond, aliphatic carbon-carbon triple bond, aromatic formyl group and aromatic nitro group is subjected to a wet hydrogenation treatment in the presence of the above selective hydrogenation catalyst, thereby hydrogenating the functional group in a substantially selective manner.

By using a functional group-selective hydrogenation catalyst and hydrogenation method of the present invention, one or more functional groups selected from the group consisting of an aliphatic carbon-carbon double bond, aliphatic carbon-carbon triple bond, aromatic formyl group and aromatic nitro group within an organic compound is selectively hydrogenated, and even if the organic compound also contains other functional groups such as an aromatic ring-bonded halogen atom, O-benzyl group, aromatic ketonic carbonyl group, N-benzyloxycarbonyl group and/or aromatic nitrile group, these functional groups undergo no substantial hydrogenation or hydrogenolysis.

DETAILED DESCRIPTION OF THE PREFERRED EMBODIMENTS

As follows is a more detailed description of the present invention. Within the scope of the claims and the description of the present application, the terms listed below have the meanings detailed below.

"Aromatic formyl group": a formyl group that forms part of an aromatic aldehyde, wherein the carbon atom to which the formyl group is bonded is a member of an aromatic carbocyclic or heterocyclic ring.

"Aromatic nitro group": a nitro group bonded to an aromatic hydrocarbon ring or heterocyclic ring.

"Aromatic ring-bonded halogen atom": a halogen atom bonded to an aromatic carbocyclic or heterocyclic ring.

"Aromatic ketonic carbonyl group": a carbonyl group that forms part of a ketone, wherein at least one of the two carbon atoms to which the carbonyl group is bonded is a member of an aromatic carbocyclic or heterocyclic ring.

"O-benzyl group": a benzyl group bonded to an oxygen atom (O).

"N-benzyloxycarbonyl group": a benzyloxycarbonyl group bonded to a nitrogen atom (N).

"Aromatic nitrile group": a nitrile group (—CN) bonded to an aromatic hydrocarbon ring or heterocyclic ring.

There are no particular restrictions on the method used for producing the functional group-selective hydrogenation catalyst of the present invention, although the catalyst is usually produced by supporting the organic sulfur compound on a palladium catalyst that comprises palladium supported on a carrier.

Examples of suitable carriers include alumina, silica, silica-alumina, and carbon-based carriers, and of these, carbon-based carriers such as carbon black or activated carbon are preferred, and activated carbon is particularly desirable.

Although there are no particular restrictions on the specific surface area of the carrier, the value is preferably within a range from 50 to 3,000 M2/g, and even more preferably from 100 to 1,500 m²/g.

Furthermore, although there are no particular restrictions on the particle size of the carrier, the median diameter is preferably within a range from 0.5 to 500 µm, and even more preferably from 5 to 500 µm.

Production of the palladium catalyst can be conducted, for example, by dissolving a palladium compound in a solvent, and then adding the carrier to the solution, thereby causing the palladium compound to adsorb to, or become impregnated within, the carrier. In those cases where the palladium compound is a water-soluble compound such as chloropalladic acid, water can be used as the solvent. In those cases where the palladium compound is a water-insoluble compound such as bis(2,4-pentanedionato)palladium, an organic solvent capable of dissolving the palladium compound is used to effect the adsorption or impregnation. A catalyst in which palladium has been supported on a carrier using a method such as adsorption or impregnation may be subjected to a reduction treatment if required. In the case of a wet reduction, either a reducing agent such as methanol, formaldehyde or formic acid, or gaseous hydrogen can be used. In the case of a dry reduction, gaseous hydrogen is used, although the hydrogen gas may also be diluted with an inert gas such as nitrogen.

There are no particular restrictions on the organic sulfur compound provided it is an organic compound that includes a sulfur atom having a lone pair of electrons, and suitable examples include organic sulfur compounds represented by a general formula (I) shown below:

$$R_1\text{—}S\text{—}R_2 \qquad (I)$$

(wherein, $R_1$ and $R_2$ each represent a hydrogen atom, an alkyl group or alkenyl group of to 12 carbon atoms, or an aryl group of 6 to 8 carbon atoms, or alternatively, $R_1$ and $R_2$ may be bonded together to form an alkylene or alkadienylene group of 2 to 6 carbon atoms, provided $R_1$ and $R_2$ are not both hydrogen atoms), as well as alcohols containing a sulfur atom having a lone pair of electrons such as 2-mercaptoethanol, 3-mercapto-1-propanol and 6-mercapto-1-hexanol, carboxylic acids containing a sulfur atom having a lone pair of electrons such as thiomalic acid and thiolactic acid, amines containing a sulfur atom having a lone pair of electrons such as 2-mercaptoethylamine, 3-mercapto-1-propylamine and thiourea, amino acids containing a sulfur atom having a lone pair of electrons such as cysteine, methionine and cystine, and heterocyclic compounds containing a sulfur atom having a lone pair of electrons such as 1,3-thiazole, 1,3,4-thiadiazole and ethylenethiourea. Of these, organic compounds represented by the general formula (I) are preferred.

There are no particular restrictions on the compounds represented by the general formula (I), and suitable examples include di-n-butyl sulfide, di-tert-butyl sulfide, di-n-hexyl sulfide, di-n-octyl sulfide, di-(2-ethylhexyl)sulfide, dodecanethiol, diphenyl sulfide, tetrahydrothiofuran and thiophene, and of these, diphenyl sulfide is particularly preferred.

Although there are no particular restrictions on the palladium catalyst onto which the organic sulfur compound is jointly supported, preferred catalysts include palladium-alumina catalysts, palladium-silica catalysts, palladium-silica-alumina catalysts and palladium-carbon catalysts, and palladium-carbon catalysts are particularly desirable.

The method used for jointly supporting the organic sulfur compound on the palladium catalyst is a wet method, namely, is conducted within a solvent. Although there are no particular restrictions on the solvent used during this supporting process, a solvent capable of dissolving the organic sulfur compound is preferred. Water is preferred as the solvent for water-soluble organic sulfur compounds, whereas in the case of water-insoluble organic sulfur compounds, suitable solvents include alcohols such as methanol and ethanol, ketones such as acetone and 2-butanone, ethers such as diethyl ether, tert-butyl methyl ether and tetrahydrofuran, aromatic solvents such as benzene and toluene, and aliphatic hydrocarbons such as hexane and octane.

There are no particular restrictions on the quantity of the organic sulfur compound jointly supported on the palladium catalyst, but a sulfur/palladium molar ratio within a range from 0.01 to 10 is preferred, and ratios from 0.1 to 3 are particularly desirable. If this ratio is smaller than the above range, then the functional group hydrogenation selectivity tends to diminish, whereas if the ratio is larger than the above range, the hydrogenation activity tends to weaken.

Although there are no particular restrictions on the temperature used during the process of jointly supporting the organic sulfur compound on the palladium catalyst, a temperature within a range from room temperature (20° C., this also applies to subsequent references to room temperature) to the boiling point of the solvent is ideal.

Although there are no particular restrictions on the palladium content of the palladium catalyst, the quantity is preferably within a range from 1 to 50% by weight, and even more preferably from 5 to 20% by weight. Furthermore, there are no particular restrictions on the physical form of the palladium catalyst, although powdered or granulated catalysts are preferred, and powdered catalysts are particularly desirable.

The palladium catalyst with the organic sulfur compound supported jointly thereon can be separated from the solvent by a method such as filtration. If required, the isolated catalyst may be washed and dried, thereby completing production of a functional group-selective hydrogenation catalyst of the present invention.

A functional group-selective hydrogenation method of the present invention is conducted by bringing a substrate having at least one functional group selected from the group consisting of an aromatic ring-bonded halogen atom, O-benzyl group, aromatic ketonic carbonyl group, N-benzyloxycarbonyl group and aromatic nitrile group, and also having at least one functional group selected from the group consisting of an aliphatic carbon-carbon double bond, aliphatic carbon-carbon triple bond, aromatic formyl group and aromatic nitro group, into contact with hydrogen in the presence of a palladium-carbon catalyst with the organic sulfur compound supported jointly thereon.

Examples of compounds (substrates) that can be targeted by the functional group-selective hydrogenation method of the present invention include compounds having at least one functional group selected from the group consisting of an aromatic ring-bonded halogen atom, O-benzyl group, aromatic ketonic carbonyl group, N-benzyloxycarbonyl group and aromatic nitrile group, and also having at least one functional group selected from the group consisting of an aliphatic carbon-carbon double bond, aliphatic carbon-carbon triple bond, aromatic formyl group and aromatic nitro group, and specific examples of suitable target compounds include the O-benzyl-protected compounds dibenzyl trans-stilbene-4,4- dicarboxylate and benzyl 5-hexynoate, although the present invention is in no way limited to these examples.

Furthermore, these compounds that function as substrates may also include other functional groups besides the aromatic ring-bonded halogen atom, O-benzyl group, aromatic ketonic carbonyl group, N-benzyloxycarbonyl group, aromatic nitrile group, or the carbon-carbon double bond, carbon-carbon triple bond, aromatic formyl group or aromatic nitro group.

The functional group-selective hydrogenation method of the present invention is conducted as a wet method, namely, within a solvent. Although there are no particular restrictions on the solvent, solvents capable of dissolving the reaction substrate are preferred. Water is preferred as the solvent for water-soluble reaction substrates, whereas in the case of water-insoluble reaction substrates, suitable solvents include alcohols such as methanol and ethanol, ketones such as acetone and 2-butanone, ethers such as diethyl ether, tert-butyl methyl ether and tetrahydrofuran, aromatic solvents such as benzene and toluene, and aliphatic hydrocarbons such as hexane and octane.

There are no particular restrictions on the reaction temperature employed for the functional group-selective hydrogenation method of the present invention, although a temperature within a range from room temperature (20° C., this also applies below) to the boiling point of the solvent is ideal.

Furthermore, the functional group-selective hydrogenation method of the present invention requires the presence of hydrogen. This hydrogen is free-state hydrogen, and is typically supplied to the reaction, or supplied to the reaction system prior to the reaction, in the form of hydrogen gas. For example, the hydrogen gas may be supplied to the gaseous phase located above the stirred reaction solution, or may be bubbled through the reaction solution. The hydrogen gas may also be supplied as a mixed gas with an inert gas such as nitrogen. Although there are no particular restrictions on the pressure of hydrogen supplied, the partial pressure of hydrogen is preferably within a range from 0.05 to 100 atmospheres, and even more preferably from 0.5 to 10 atmospheres. Following completion of the reaction, the used catalyst can be separated from the solution containing the reaction product by a simple method such as filtration.

EXAMPLES

As follows is a description of examples of the present invention, although the present invention is in no way limited by the following examples.

Example 1

Preparation of a Palladium-Carbon Catalyst with diphenyl sulfide Supported Jointly Thereon Into a round-bottomed flask that had been flushed with argon was weighed 532.1 mg of a 10% by weight palladium-carbon powdered K-type catalyst (manufactured by N.E. Chemcat Corporation), and 10 ml of methanol was then added to the flask. Subsequently, 186.3 mg of diphenyl sulfide was added, and the resulting mixture was stirred for 5 days under an argon atmosphere. The catalyst was then isolated by filtration, washed with 10 ml of methanol and then 10 ml of ether, and was then dried in a desiccator, yielding a palladium-carbon catalyst with diphenyl sulfide supported jointly thereon.

Example 2

Functional Group-Selective Hydrogenation of 1,5-diphenyl-2,4-pentadien-1-one Using the Palladium-Carbon Catalyst with diphenyl sulfide Supported Jointly Thereon 100 mg of 1,5-diphenyl-2,4-pentadien-1-one, which is a compound that includes both an aromatic ketonic carbonyl group and aliphatic carbon-carbon double bonds, was dissolved in 1 ml of methanol, and 10 mg of the palladium-carbon catalyst impregnated with diphenyl sulfide prepared in the example 1 was then added to the solution. Reaction under slight hydrogen pressurization using a balloon was then conducted for 3 hours at room temperature. Following removal of the catalyst by filtration, the reaction products were identified by gas chromatographic analysis of the reaction solution. The selectivity for 1,5-diphenylpentan-1-one, which represents the product arising from hydrogenation of only the carbon-carbon double bonds, was 95%, whereas the selectivity for 1,5-diphenylpentan-1-ol, which represents the product arising from hydrogenation of both the aromatic ketonic carbonyl group and the carbon-carbon double bonds, was 5%.

Example 3

Functional Group-Selective Hydrogenation of benzyl 3-phenylacrylate Using the Palladium-Carbon Catalyst with Diphenyl Sulfide Supported Jointly Thereon With the exceptions of replacing the 1,5-diphenyl-2,4-pentadien-1-one from the example 2 with benzyl 3-phenylacrylate, which represents a compound containing r double bond and an O-benzyl group of a benzyl carboxylate ester, and altering the reaction time to 24 hours, a hydrogenation was conducted and the reaction products were identified in the same manner as the example 2. The selectivity for benzyl 3-phenylpropionate, which represents the product arising from hydrogenation of only the carbon-carbon double bond, was 100%, whereas the selectivity for 3-phenylpropionic acid, which represents the product arising from hydrogenation of the carbon-carbon double bond and hydrogenolysis of the O-benzyl group of the benzyl carboxylate ester, was 0%.

Example 4

Functional Group-Selective Hydrogenation of 1,3-diphenyl-2-propen-1-one Using the Palladium-Carbon Catalyst with diphenyl sulfide Supported Jointly Thereon With the exceptions of replacing the 1,5-diphenyl-2,4-pentadien-1-one from the example 2 with 1,3-diphenyl-2-propen-1-one, which represents a compound containing an aliphatic carbon-carbon double bond and an aromatic ketonic carbonyl group, and altering the reaction time to 23 hours, a hydrogenation was conducted and the reaction products were identified in the same manner as the example 2. The selectivity for 1,3-diphenylpropan-1-one, which represents the product arising from hydrogenation of only the carbon-carbon double bond, was 100%, whereas the selectivity for 1,3- diphenylpropan-1-ol, which represents the product arising from hydrogenation of both the carbon-carbon double bond and the aromatic ketonic carbonyl group, was 0%.

Example 5

Functional Group-Selective Hydrogenation of 1-(4-chlorophenyl)-3-phenyl-2-propen-1-one Using the Palladium-Carbon Catalyst with Diphenyl Sulfide Supported Jointly Thereon With the exceptions of replacing the 1,5-diphenyl-2,4-pentadien-1-one from the example 2 with 1-(4-chlorophenyl)-3-phenyl-2-propen-1-one, which represents a compound containing an aliphatic carbon-carbon double bond, an aromatic ketonic carbonyl group and an aromatic ring-bonded halogen atom, and altering the reaction time to 23 hours, a hydrogenation was conducted and the reaction products were identified in the same manner as the example 2. The selectivity for 1-(4-chlorophenyl)-3-phenylpropan-1-one, which represents the product arising from hydrogenation of only the carbon-carbon double bond, was 100%, whereas the selectivity for 1-(4-chlorophenyl)-3-phenylpropan-1-ol, which represents the product arising from hydrogenation of both the carbon-carbon double bond and the aromatic ketonic carbonyl group, was 0%, and the selectivity for 1,3-diphenylpropan-1-ol, which represents the product arising from hydrogenation of both the carbon-carbon double bond and the aromatic ketonic carbonyl group, as well as hydrogenolysis of the aromatic ring-bonded halogen atom, was also 0%.

Example 6

Functional Group-Selective Hydrogenation of 2-allyl-4-hydroxyacetophenone Using the Palladium-Carbon Catalyst with Diphenyl Sulfide Supported Jointly Thereon With the exceptions of replacing the 1,5-diphenyl-2,4-pentadien-1-one from the example 2 with 2-allyl-4-hydroxyacetophenone, which represents a compound containing an aliphatic carbon-carbon double bond and an aromatic ketonic carbonyl group, and altering the reaction time to 24 hours, a hydrogenation was conducted and the reaction products were identified in the same manner as the example 2. The selectivity for 2-propyl-4-hydroxyacetophenone, which represents the product arising from hydrogenation of only the carbon-carbon double bond, was 100%, whereas the selectivity for 4-(1-hydroxyethyl)-3-propylphenol, which represents the product arising from hydrogenation of both the carbon-carbon double bond and the aromatic ketonic carbonyl group, was 0%.

Example 7

Functional Group-Selective Hydrogenation of 3-allyl-2,4-dihydroxy-5-benzoylbenzophenone Using the Palladium-Carbon Catalyst with Diphenyl Sulfide Supported Jointly Thereon With the exceptions of replacing the 1,5-diphenyl-2,4-pentadien-1-one from the example 2 with 3-allyl-2,4-dihydroxy-5-benzoylbenzophenone, which represents a compound containing an aliphatic carbon-carbon double bond and aromatic ketonic carbonyl groups, and altering the reaction time to 24 hours, a hydrogenation was conducted and the reaction products were identified in the same manner as the example 2. The selectivity for 3-propyl-2,4-dihydroxy-5-benzoylbenzophenone, which represents the product arising from hydrogenation of only the carbon-carbon double bond, was 100%, whereas the selectivity for 3-propyl-2,4-dihydroxy-5-(phenylhydroxymethyl)benzophenone, which represents the product arising from hydrogenation of the carbon-carbon double bond and one of the aromatic ketonic carbonyl groups, was 0%, and the selectivity for 3-propyl-2,4-dihydroxy-1,5-bis(phenylhydroxymethyl)benzene, which represents the product arising from hydrogenation of the carbon-carbon double bond and both of the aromatic ketonic carbonyl groups, was also 0%.

Example 8

Functional Group-Selective Hydrogenation of 1,4-diphenyl-2-buten-1,4-dione Using the Palladium-Carbon Catalyst with Diphenyl Sulfide Supported Jointly Thereon With the exceptions of replacing the 1,5-diphenyl-2,4-pentadien-1-one from the example 2 with 1,4-diphenyl-2-buten-1,4-dione, which represents a compound containing an aliphatic carbon-carbon double bond and aromatic ketonic carbonyl groups, and altering the reaction time to 24 hours, a hydrogenation was conducted and the reaction products were identified in the same manner as the example 2. The selectivity for 1,4-diphenylbutan-1,4-dione, which represents the product arising from hydrogenation of only the carbon-carbon double bond, was 100%, whereas the selectivity for 1,4-diphenyl-4-hydroxybutan-1-one, which represents the product arising from hydrogenation of the carbon-carbon double bond and one of the aromatic ketonic carbonyl groups, was 0%, and the selectivity for 1,4-diphenylbutan-1,4-diol, which represents the product arising from hydrogenation of the carbon-carbon double bond and both of the aromatic ketonic carbonyl groups, was also 0%.

Example 9

Functional Group-Selective Hydrogenation of 1,3-diphenyl-2-propyn-1-one Using the Palladium-Carbon Catalyst with Diphenyl Sulfide Supported Jointly Thereon With the exceptions of replacing the 1,5-diphenyl-2,4-pentadien-1-one from the example 2 with 1,3-diphenyl-2-propyn-1-one, which represents a compound containing an aliphatic carbon-carbon triple bond and an aromatic ketonic carbonyl group, and altering the reaction time to 24 hours, a hydrogenation was conducted and the reaction products were identified in the same manner as the example 2. The selectivity for 1,3-diphenyl-1-propanone, which represents the product arising from hydrogenation of only the carbon-carbon triple bond, was 72%, whereas the selectivity for 1,3-diphenyl-1-propanol, which represents the product arising from hydrogenation of both the carbon-carbon triple bond and the aromatic ketonic carbonyl group, was 28%.

Example 10

Functional Group-Selective Hydrogenation of benzyl methacrylate Using the Palladium-Carbon Catalyst with Diphenyl Sulfide Supported Jointly Thereon With the exceptions of replacing the 1,5-diphenyl-2,4-pentadien-1-one from the example 2 with benzyl methacrylate, which represents a compound containing an aliphatic carbon-carbon double bond and an O-benzyl group of a benzyl ester, altering the reaction time to 24 hours, and altering the analysis method from gas chromatography to $^1$H-NMR, a hydrogenation was conducted in the same manner as the example 2, and the reaction products were then identified. The selectivity for benzyl 2-methylpropionate, which represents the product arising from hydrogenation of only the carbon-carbon double bond, was 100%, whereas the selectivity for 2-methylpropionic acid, which represents the product arising from hydrogenation of the carbon-carbon double bond and hydrogenolysis of the O-benzyl group of the benzyl ester, was 0%.

Example 11

Functional Group-Selective Hydrogenation of benzyl acrylate Using the Palladium-Carbon Catalyst with Diphenyl Sulfide Supported Jointly Thereon With the exceptions of replacing the benzyl methacrylate from the example 10 with benzyl acrylate, a hydrogenation was conducted and the reaction products were identified in the same manner as the example 10. The selectivity for benzyl propionate, which represents the product arising from hydrogenation of only the carbon-carbon double bond, was 100%, whereas the selectivity for propionic acid, which represents the product arising from hydrogenation of the carbon-carbon double bond and hydrogenolysis of the O-benzyl group of the benzyl ester, was 0%.

Example 12

Functional Group-Selective Hydrogenation of dibenzyl trans-stilbene-4,4'-dicarboxylate Using the Palladium-Carbon Catalyst with Diphenyl Sulfide Supported Jointly Thereon With the exceptions of replacing the 1,5-diphenyl-2,4-pentadien-1-one from the example 2 with dibenzyl trans-stilbene-4,4'-dicarboxylate, which represents a compound containing an aliphatic carbon-carbon double bond and O-benzyl groups of benzyl esters, and altering the reaction time to 24 hours, a hydrogenation was conducted and the reaction products were identified in the same manner as the example 2. The selectivity for dibenzyl bibenzyl-4,4'-dicarboxylate, which represents the product arising from hydrogenation of only the carbon-carbon double bond, was 100%, whereas the selectivity for bibenzyl-4,4'-dicarboxylic acid monobenzyl ester, which represents the product arising from hydrogenation of the carbon-carbon double bond and hydrogenolysis of one of the O-benzyl groups of the benzyl esters, was 0%, and the selectivity for bibenzyl-4,4'-dicarboxylic acid, which represents the product arising from hydrogenation of the carbon-carbon double bond and hydrogenolysis of both of the O-benzyl groups of the benzyl esters, was also 0%.

Example 13

Functional Group-Selective Hydrogenation of benzyl 5-hexynoate Using the Palladium-Carbon Catalyst with Diphenyl Sulfide Supported Jointly Thereon With the exceptions of replacing the 1,5-diphenyl-2,4-pentadien-1-one from the example 2 with benzyl 5-hexynoate, which represents a compound containing an aliphatic carbon-carbon triple bond and an O-benzyl group of a benzyl ester, and altering the reaction time to 24 hours, a hydrogenation was conducted and the reaction products were identified in the same manner as the example 2. The selectivity for benzyl hexanoate, which represents the product arising from hydrogenation of only the carbon-carbon triple bond, was 100%, whereas the selectivity for hexanoic acid, which represents the product arising from hydrogenation of the carbon-carbon triple bond and hydrogenolysis of the O-benzyl group of the benzyl ester, was 0%.

Example 14

Functional Group-Selective Hydrogenation of diallylbenzyloxycarbonylamine Using the Palladium-Carbon Catalyst with Diphenyl Sulfide Supported Jointly Thereon With the exceptions of replacing the 1,5-diphenyl-2,4-pentadien-1-one from the example 2 with diallylbenzyloxycarbonylamine, which represents a compound containing aliphatic carbon-carbon double bonds and a N-benzyloxycarbonyl group, and altering the reaction time to 24 hours, a hydrogenation was conducted and the reaction products were identified in the same manner as the example 2. The selectivity for dipropylbenzyloxycarbonylamine, which represents the product arising from hydrogenation of only the carbon-carbon double bonds, was 100%, whereas the selectivity for dipropylamine, which represents the product arising from hydrogenation of the carbon-carbon double bonds and hydrogenolysis of the N-benzyloxycarbonyl group, was 0%.

Example 15

Functional Group-Selective Hydrogenation of ethyl 3-{4-(N-benzyloxycarbonyl)aminophenyl}-2-propenoate Using the Palladium-Carbon Catalyst with Diphenyl Sulfide Supported Jointly Thereon With the exceptions of replacing the 1,5-diphenyl-2,4-pentadien-1-one from the example 2 with ethyl 3-{4-(N-benzyloxycarbonyl)aminophenyl}-2-propenoate, which represents a compound containing an aliphatic carbon-carbon double bond and a N-benzyloxycarbonyl group, and altering the reaction time to 24 hours, a hydrogenation was conducted and the reaction products were identified in the same manner as the example 2. The selectivity for ethyl 3-{4-(N-benzyloxycarbonyl)aminophenyl}-propionate, which represents the product arising from hydrogenation of only the carbon-carbon double bond, was 98%, whereas the selectivity for ethyl 3-(4-aminophenyl)-propionate, which represents the product arising from hydrogenation of the carbon-carbon double bond and hydrogenolysis of the N-benzyloxycarbonyl group, was 2%.

Example 16

Functional Group-Selective Hydrogenation of 2-(N-benzyloxycarbonyl)aminobenzyl acrylate Using the Palladium-Carbon Catalyst with Diphenyl Sulfide Supported Jointly Thereon With the exceptions of replacing the 1,5-diphenyl-2,4-pentadien-1-one from the example 2 with 2-(N-benzyloxycarbonyl)aminobenzyl acrylate, which represents a compound containing an aliphatic carbon-carbon double bond and a N-benzyloxycarbonyl group, and altering the reaction time to 24 hours, a hydrogenation was conducted and the reaction products were identified in the same manner as the example 2.

The selectivity for 2-(N-benzyloxycarbonyl)aminobenzyl propionate, which represents the product arising from hydrogenation of only the carbon-carbon double bond, was 100%, whereas the selectivity for 2-aminobenzyl propionate, which represents the product arising from hydrogenation of the carbon-carbon double bond and hydrogenolysis of the N-benzyloxycarbonyl group, was 0%.

Example 17

Functional Group-Selective Hydrogenation of N-allyl-N-benzyloxycarbonylaniline Using the Palladium-Carbon Catalyst with Diphenyl Sulfide Supported Jointly Thereon With the exceptions of replacing the 1,5-diphenyl-2,4-pentadien-1-one from the example 2 with N-allyl-N-benzyloxycarbonylaniline, which represents a compound containing an aliphatic carbon-carbon double bond and a N-benzyloxycarbonyl group, and altering the reaction time to 24 hours, a hydrogenation was conducted and the reaction products were identified in the same manner as the example 2. The selectivity for N-propyl-N-benzyloxycarbonylaniline, which represents the product arising from hydrogenation of only the carbon-carbon double bond, was 100%, whereas the selectivity for N-propylaniline, which represents the product arising from hydrogenation of the carbon-carbon double bond and hydrogenolysis of the N-benzyloxycarbonyl group, was 0%.

Example 18

Functional Group-Selective Hydrogenation of 3-phenyl-2-propenyl N-benzyloxycarbonylanthranilate Using the Palladium-Carbon Catalyst with Diphenyl Sulfide Supported Jointly Thereon With the exceptions of replacing the 1,5-diphenyl-2,4-pentadien-1-one from the example 2 with 3-phenyl-2-propenyl N-benzyloxycarbonylanthranilate, which represents a compound containing an aliphatic carbon-carbon double bond and a N-benzyloxycarbonyl group, and altering the reaction time to 24 hours, a hydrogenation was conducted and the reaction products were identified in the same manner as the example 2. The selectivity for 3-phenyl-2-propyl N-benzyloxycarbonylanthranilate, which represents the product arising from hydrogenation of only the carbon-carbon double bond, was 100%, whereas the selectivity for 3-phenyl-2-propyl anthranilate, which represents the product arising from hydrogenation of the carbon-carbon double bond and hydrogenolysis of the N-benzyloxycarbonyl group, was 0%.

Example 19

Functional Group-Selective Hydrogenation of p-nitrobenzophenone Using the Palladium-Carbon Catalyst with Diphenyl Sulfide Supported Jointly Thereon With the exceptions of replacing the 1,5-diphenyl-2,4-pentadien-1-one from the example 2 with p-nitrobenzophenone, which represents a compound containing an aromatic nitro group and an aromatic ketonic carbonyl group, and altering the reaction time to 24 hours, a hydrogenation was conducted and the reaction products were identified in the same manner as the example 2. The selectivity for p-aminobenzophenone, which represents the product arising from hydrogenation of only the aromatic nitro group, was 100%, whereas the selectivity for 4-(1-hydroxyethyl)aniline, which represents the product arising from hydrogenation of both the aromatic nitro group and the aromatic ketonic carbonyl group, was 0%.

Example 20

Functional Group-Selective Hydrogenation of 1-(4-nitrophenyl)-3-phenyl-2-propen-1-one Using the Palladium-Carbon Catalyst with Diphenyl Sulfide Supported Jointly Thereon With the exceptions of replacing the 1,5-diphenyl-2,4-pentadien-1-one from the example 2 with 1-(4-nitrophenyl)-3-phenyl-2-propen-1-one, which represents a compound containing an aromatic nitro group, an aliphatic carbon-carbon double bond and an aromatic ketonic carbonyl group, and altering the reaction time to 24 hours, a hydrogenation was conducted and the reaction products were identified in the same manner as the example 2. The selectivity for 1-(4-aminophenyl)-3-phenylpropan-1-one, which represents the product arising from hydrogenation of only the aromatic nitro group and the carbon-carbon double bond, was 100%, whereas the selectivity for 1-(4-aminophenyl)-3-phenylpropan-1-ol, which represents the product arising from hydrogenation of the aromatic nitro group, the carbon-carbon double bond and the aromatic ketonic carbonyl group, was 0%.

Example 21

Functional Group-Selective Hydrogenation of 3-phenylacrylonitrile Using the Palladium-Carbon Catalyst with Diphenyl Sulfide Supported Jointly Thereon With the exceptions of replacing the 1,5-diphenyl-2,4-pentadien-1-one from the example 2 with 3-phenylacrylonitrile, which represents a compound containing an aliphatic carbon-carbon double bond and a nitrile group, and altering the reaction time to 24 hours, a hydrogenation was conducted and the reaction products were identified in the same manner as the example 2. The selectivity for 3-phenylpropionitrile, which represents the product arising from hydrogenation of only the carbon-carbon double bond, was 100%, whereas the selectivity for 3-phenyl-1-propylamine, which represents the product arising from hydrogenation of both the carbon-carbon double bond and the nitrile group, was 0%.

Comparative Example 1

Hydrogenation of 1,5-diphenyl-2,4-pentadien-1-one Using a Palladium-Carbon Catalyst 100 mg of 1,5-diphenyl-2,4-pentadien-1-one, which is a compound that includes both an aromatic ketonic carbonyl group and aliphatic carbon-carbon double bonds, was dissolved in 1 ml of methanol, and 10 mg of a 10% by weight palladium-carbon powdered K-type catalyst (manufactured by N.E. Chemcat Corporation) was then added to the solution. Reaction under slight hydrogen pressurization using a balloon was then conducted for 3 hours at room temperature. Following removal of the catalyst by filtration, the reaction products were identified by gas chromatographic analysis of the reaction solution. The selectivity for 1,5-diphenylpentan-1-one, which represents the product arising from hydrogenation of only the carbon-carbon double bonds, was 0%, whereas the selectivity for 1,5-diphenylpentan-1-ol, which represents the product arising from hydrogenation of both the aromatic ketonic carbonyl group and the carbon-carbon double bonds, was 100%.

Comparative Example 2

Hydrogenation of benzyl 3-phenylacrylate Using a Palladium-Carbon Catalyst 100 mg of benzyl 3-phenylacrylate, which is a compound that includes both an O-benzyl group of a benzyl ester and an aliphatic carbon-carbon double bond, was dissolved in 1 ml of methanol, and 10 mg of a 10% by weight palladium-carbon powdered K-type catalyst (manufactured by N.E. Chemcat Corporation) was then added to the solution. Reaction under slight hydrogen pressurization using a balloon was then conducted for 24 hours at room temperature. Following removal of the catalyst by filtration, the reaction products were identified by gas chromatographic analysis of the reaction solution. The selectivity for benzyl 3-phenylpropionate, which represents the product arising from hydrogenation of only the carbon-carbon double bond, was 0%, whereas the selectivity for 3-phenylpropionic acid, which represents the product arising from hydrogenation of the carbon-carbon double bond and hydrogenolysis of the O-benzyl group of the benzyl ester, was 100%.

Comparative Example 3

Hydrogenation of 1,5-diphenyl-2,4-pentadien-1-one Using a Palladium-Carbon Catalyst with Ethylenediamine Supported Jointly Thereon 100 mg of 1,5-diphenyl-2,4-pentadien-1-one, which is a compound that includes both an aromatic ketonic carbonyl group and aliphatic carbon-carbon double bonds, was dissolved in 1 ml of methanol, and 10 mg of a 10% by weight palladium-carbon powder with ethylenediamine supported jointly thereon (manufactured by Wako Pure Chemical Industries, Ltd.) was then added to the solution. Reaction under slight hydrogen pressurization using a balloon was then conducted for 3 hours at room temperature. Following removal of the catalyst by filtration, the reaction products were identified by gas chromatographic analysis of the reaction solution. The selectivity for 1,5-diphenylpentan-1-one, which represents the product arising from hydrogenation of only the carbon-carbon double bonds, was 0%, whereas the selectivity for 1,5-diphenylpentan-1-ol, which represents the product arising from hydrogenation of both the aromatic ketonic carbonyl group and the carbon-carbon double bonds, was 100%.

Comparative Example 4

Hydrogenation of benzyl 3-phenylacrylate Using a Palladium-Carbon Catalyst with Ethylenediamine Supported Jointly Thereon 100 mg of benzyl 3-phenylacrylate, which is a compound that includes both an O-benzyl group of a benzyl ester and an aliphatic carbon-carbon double bond, was dissolved in 1 ml of methanol, and 10 mg of a 10% by weight palladium-carbon powder with ethylenediamine supported jointly thereon (manufactured by Wako Pure Chemical Industries, Ltd.) was then added to the solution. Reaction under slight hydrogen pressurization using a balloon was then conducted for 24 hours at room temperature. Following removal of the catalyst by filtration, the reaction products were identified by gas chromatographic analysis of the reaction solution. The selectivity for benzyl 3-phenylpropionate, which represents the product arising from hydrogenation of only the carbon-carbon double bond, was 0%, whereas the selectivity for 3-phenylpropionic acid, which represents the product arising from hydrogenation of the carbon-carbon double bond and hydrogenolysis of the O-benzyl group of the benzyl ester, was 100%.

INDUSTRIAL APPLICABILITY

The functional group-selective hydrogenation catalyst and functional group-selective hydrogenation method of the present invention are useful for research, development, and production within the fine chemical industry, including the production of pharmaceutical intermediates and the production of functional materials.

What is claimed is:

1. A functional group-selective hydrogenation method, comprising
subjecting an organic compound having at least one first functional group to a wet hydrogenation treatment in the presence of a selective hydrogenation catalyst, thereby hydrogenating the first functional group in a substantially selective manner;
wherein the at least one first functional group is selected from the group consisting of an aliphatic carbon-carbon double bond, an aromatic formyl group, and combinations thereof;
wherein the selective hydrogenation catalyst comprises
a carrier,
palladium, and
an organic sulfur compound; and
wherein the palladium and the organic sulfur compound are jointly supported on the carrier;
wherein the organic compound further comprises at least one second functional group selected from the group consisting of an aromatic ring-bonded halogen atom, an O-benzyl group, an aromatic ketonic carbonyl group, an N-benzyloxycarbonyl group, an aromatic nitrile group, and combinations thereof; and
wherein the second functional group undergoes no substantial hydrogenation.

2. The functional group-selective hydrogenation method according to claim 1, wherein the organic sulfur compound is a compound represented by a general formula (I) shown below:

wherein, $R_1$ and $R_2$ each represent a hydrogen atom, an alkyl group or alkenyl group of 1 to 12 carbon atoms, or an aryl group of 6 to 8 carbon atoms, or alternatively, $R_1$ and $R_2$ are bonded together to form an alkylene or alkadienylene group of 2 to 6 carbon atoms, provided $R_1$ and $R_2$ are not both hydrogen atoms.

3. The functional group-selective hydrogenation method according to claim 1, wherein said organic sulfur compound is diphenyl sulfide.

4. The method of claim 3, wherein the at least one first functional group is an aliphatic carbon-carbon double bond.

5. The functional group-selective hydrogenation method according to claim 1, wherein said selective hydrogenation catalyst consists essentially of the carrier, palladium and the organic sulfur compound.

6. The method of claim 1, wherein the at least one first functional group is an aliphatic carbon-carbon double bond.

7. The method of claim 1, wherein the at least one first functional group is an aliphatic carbon-carbon double bond, and wherein the at least one second functional group is an aromatic ring-bonded halogen atom.

8. The method of claim 1, wherein the at least one first functional group is an aliphatic carbon-carbon double bond, and wherein the at least one second functional group is an O-benzyl group.

9. The method of claim 1, wherein the at least one first functional group is an aliphatic carbon-carbon double bond, and wherein the at least one second functional group is an aromatic ketonic carbonyl group.

10. The method of claim 1, wherein the at least one first functional group is an aliphatic carbon-carbon double bond, and wherein the at least one second functional group is an N-benzyloxycarbonyl group.

11. The method of claim 1, wherein the at least one first functional group is an aliphatic carbon-carbon double bond, and wherein the at least one second functional group is an aromatic nitrile group.

12. The method of claim 1, wherein the at least one first functional group is an aromatic formyl group, and wherein the at least one second functional group is an aromatic ring-bonded halogen atom.

13. The method of claim 1, wherein the at least one first functional group is an aromatic formyl group, and wherein the at least one second functional group is an O-benzyl group.

14. The method of claim 1, wherein the at least one first functional group is an aromatic formyl group, and wherein the at least one second functional group is an aromatic ketonic carbonyl group.

15. The method of claim 1, wherein the at least one first functional group is an aromatic formyl group, and wherein the at least one second functional group is an N-benzyloxycarbonyl group.

16. The method of claim 1, wherein the at least one first functional group is an aromatic formyl group, and wherein the at least one second functional group is an aromatic nitrile group.

17. A functional group-selective hydrogenation method, comprising
subjecting an organic compound having at least one first functional group and at least one second functional group to a wet hydrogenation treatment in the presence of a selective hydrogenation catalyst, thereby hydrogenating the first functional group in a substantially selective manner without substantial hydrogenation of the second functional group;
wherein the at least one first functional group is an aliphatic carbon-carbon triple bond and the at least one second functional group is selected from the group consisting of an aromatic ring-bonded halogen atom, an O-benzyl group, an aromatic ketonic carbonyl group, an N-benzyloxycarbonyl group, and an aromatic nitrile group,
wherein the selective hydrogenation catalyst consists essentially of a carrier, palladium, and an organic sulfur compound, and
wherein the palladium and the organic sulfur compound are jointly supported on the carrier.

18. A functional group-selective hydrogenation method, comprising
subjecting an organic compound having at least one first functional group to a wet hydrogenation treatment in the presence of a selective hydrogenation catalyst, thereby hydrogenating the first functional group in a substantially selective manner;
wherein the at least one first functional group is an aromatic formyl group;
wherein the selective hydrogenation catalyst comprises
a carrier,
palladium, and
an organic sulfur compound;
wherein the palladium and the organic sulfur compound are jointly supported on the carrier.

19. The functional group-selective hydrogenation method according to claim 18, wherein the organic sulfur compound is a compound represented by a general formula (I) shown below:

$$R_1\text{—}S\text{—}R_2 \qquad (I)$$

wherein $R_1$ and $R_2$ each represent a hydrogen atom, an alkyl group or alkenyl group of 1 to 12 carbon atoms, or an aryl group of 6 to 8 carbon atoms, or alternative, $R_1$ and $R_2$ are bonded together to form an alkylene or alkadienylene group of 2 to 6 carbon atoms, provided $R_1$ and $R_2$ are not both hydrogen atoms.

20. The functional group-selective hydrogenation method according to claim 18, wherein said organic sulfur compound is diphenyl sulfide.

21. The functional group-selective hydrogenation method according to claim 18, wherein said selective hydrogenation catalyst consists essentially of the carrier, palladium and the organic sulfur compound.

22. A functional group-selective hydrogenation method, comprising
subjecting an organic compound having at least one first functional group to a wet hydrogenation treatment in the presence of a selective hydrogenation catalyst, thereby hydrogenating the first functional group in a substantially selective manner;
wherein the selective hydrogenation catalyst comprises
a carrier,
palladium, and
an organic sulfur compound; and
wherein the palladium and the organic sulfur compound are jointly supported on the carrier; and
wherein the at least one first functional group is two functional groups, and wherein the two functional groups are an aliphatic carbon-carbon double bond and an aromatic formyl group.

23. The functional group-selective hydrogenation method according to claim 22, wherein the organic sulfur compound is a compound represented by a general formula (I) shown below:

$$R_1\text{—}S\text{—}R_2 \qquad (I)$$

wherein $R_1$ and $R_2$ each represent a hydrogen atom, an alkyl group or alkenyl group of 1 to 12 carbon atoms, or an aryl group of 6 to 8 carbon atoms, or alternatively, $R_1$ and $R_2$ are bonded together to form an alkylene or alkadienylene group of 2 to 6 carbon atoms, provided $R_1$ and $R_2$ are not both hydrogen atoms.

24. The functional-group selective hydrogenation method according to claim 22, wherein said organic sulfur compound is diphenyl sulfide.

25. The functional group-selective hydrogenation method according to claim 22, wherein said selective hydrogenation catalyst consists essentially of the carrier, palladium and the organic sulfur compound.

26. A functional group-selective hydrogenation method, comprising subjecting an organic compound having at least one first functional group to a wet hydrogenation treatment in the presence of a selective hydrogenation catalyst, thereby hydrogenating the first functional group in a substantially selective manner;

wherein the at least one first functional group is selected from the group consisting of an aliphatic carbon-carbon double bond, an aromatic formyl group and combinations thereof;

wherein the selective hydrogenation catalyst comprises a carrier, palladium and an organic sulfur compound;

wherein the palladium and the organic sulfur compound are jointly supported on the carrier; and wherein the catalyst comprises the palladium in an amount of from 7.41 to 50% by weight based on the weight of the catalyst.

27. A functional group-selective hydrogenation method, comprising subjecting an organic compound having at least one first functional group to a wet hydrogenation treatment in the presence of a selective hydrogenation catalyst, thereby hydrogenating the first functional group in a substantially selective manner;

wherein the at least one first functional group is selected from the group consisting of an aliphatic carbon-carbon double bond, an aromatic formyl group and combinations thereof;

wherein the selective hydrogenation catalyst consists essentially of a carrier, palladium and an organic sulfur compound; and wherein the palladium and the organic sulfur compound are jointly supported on the carrier.

* * * * *